US006630185B2

(12) United States Patent
Arends et al.

(10) Patent No.: US 6,630,185 B2
(45) Date of Patent: Oct. 7, 2003

(54) CRYSTALLIZATION PROCESS USING ULTRASOUND

(75) Inventors: Berend Jan Arends, Vlaardingen (NL); Renoo Avinash Blindt, Sharnbrook (GB); Jo Janssen, Vlaardingen (NL); Maria Patrick, Sharnbrook (GB)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 110 days.

(21) Appl. No.: 09/902,288

(22) Filed: Jul. 10, 2001

(65) Prior Publication Data

US 2002/0031577 A1 Mar. 14, 2002

(30) Foreign Application Priority Data

Jul. 18, 2000 (GB) .............................................. 0017626
Dec. 22, 2000 (EP) ............................................ 00204709

(51) Int. Cl.⁷ ................................................. A23D 9/00
(52) U.S. Cl. ....................... 426/238; 426/239; 426/495; 426/524; 426/601
(58) Field of Search ................................ 426/495, 238, 426/237, 601, 524; 117/5, 77, 927; 23/295 R, 306, 298, 308 R (56) References Cited

U.S. PATENT DOCUMENTS

| 4,438,149 A | 3/1984 | Verhagen et al. |
| 4,594,194 A | 6/1986 | Dieffenbacher |
| 5,209,879 A | 5/1993 | Redding, Jr. |
| 6,416,801 B2 * | 7/2002 | Beckett .................. 426/237 |
| 2002/0001647 A1 * | 1/2002 | Beckett .................. 426/237 |

FOREIGN PATENT DOCUMENTS

| EP | 0 613 620 A2 | 9/1994 |
| EP | 0 619 139 A1 | 10/1994 |
| EP | 0 765 605 A1 | 4/1997 |
| EP | 0 765 606 A1 | 4/1997 |
| WO | 92/20420 | 11/1992 |

OTHER PUBLICATIONS

Caplus Abstract 126:13, 170.*
Derwent Acc No. 1986–161,394.*
Derwent Acc No: 1985–268,356.*
International Search Report on International Application No. PCT/EP 01/08022 dated Oct. 25, 2001.
Hamm, Trans. IChemE. 74C, 1996, 61.
Kapustin, The effects of ultrasound on the kinetics of crystallisation; Consultants Bureau, New York, 1963.
Hem, The effect of ultrasonic vibrations on crystallisation processes; Ultrasonics, Oct. 1967, p. 202.
Kallies, Zur gezielten Suspensionserzeugung für die Konfektionierung von Schmelzen; PhD Thesis, Bremen 1995.
Leighton T.G., The principles of cavitation; chapter 9 in "Ultrasound in Food Processing", (Povey & Mason, eds.) Blackie Academic & Professional, London (1998).
Crum L.A., Sonoluminescence, sonochemistry and sonophysics, J. Acoust. Soc. Am. 95(1), 1994, 559.
Apfel R.E., Holland C.K., Gauging the likelihood of cavitation from short–pulse low–duty cycle diagnostic ultrasound, Ultrasound Med. Biol. 17, 1991, 179.
Internetsite http://www.aeat.com/sono/ , particularly "How does it work" under "Frequently Asked Questions". Printed on Mar. 21, 2001.
Gélat P., Hodnett M, Zeqiri B., Establishing a reference ultrasonic cleaning vessel: part 1: Supporting infrastructure and early measurements, National Physical Laboratory Report CMAM 55, Sep. 2000.

* cited by examiner

*Primary Examiner*—Carolyn Paden
(74) *Attorney, Agent, or Firm*—Gerard J. McGowan (57) ABSTRACT

The present invention relates to a process for the crystallization of a solid phase from a liquid, characterized in that the liquid during crystallization is subjected to ultrasound in the absence of transient cavitation. In particular the liquid is sonicated under such conditions of time and frequency that nucleation of stable crystals in the liquid is induced without exceeding the cavitation threshold and the occurrence of transient cavitation and the accompanying flavor deterioration is avoided. The liquid preferably is a triglyceride oil such as a vegetable oil or animal fat, e.g. liquefied milk fat.

11 Claims, 6 Drawing Sheets

CRYSTALLIZATION PROCESS USING ULTRASOUND

The present invention relates to a process where a liquefied or dissolved substance is crystallized from a melt or a solution while exposing it to ultrasound. A triglyceride fat (three fatty acid residues connected to a glycerol backbone) in particular is the subject of the present crystallisation process.

The triglyceride fats used for the manufacture of food compositions often are desired to show a specific melting behaviour. Fats as obtained from natural sources usually do not have suitable melting properties. Therefore they have to be subjected to a modification treatment. Fat fractionation is such a modification treatment. Fat fractionation consists of the physical separation of a triglyceride mixture into two or more fractions with different melting or solubility ranges. "Wet" fractionation comprises dissolving the triglyceride mixture in a hot organic solvent (e.g. hexane) and then cooling it slowly until a part (fraction) of the fat crystallizes from the solution.

Alternatively, "dry" fractionation does not make use of a solvent and comprises cooling a liquid fat slowly. Optionally a triglyceride mixture is first fully liquefied if it is solid. The fat fraction with the highest melting range will crystallize first during cooling.

The final stage of both wet and dry fractionation is separation of the crystallized ("stearin") fraction and the still liquid ("olein") fraction by filtration.

Dry fractionation is the preferred option when a "non-chemical" modification treatment is desired. For dairy fats it is the only acceptable option in terms of retaining flavour quality. However, dry fractionation is a less efficient and controllable method than wet fractionation (Ref.1).

The filter cake resulting from wet fractionation may contain as little as 2 wt. % entrapped liquid fraction (also denoted as 98% SE (separation efficiency)). The good result is due to a more favourable crystal morphology and to washing the crystallized fraction with clean solvent. By contrast, the solids content in the cake resulting from a standard dry fractionation process typically is at most about 60% (60% SE), the remaining 40% being entrapped olein.

Crystal habit modifiers (CHM's) when added to the melt modify the crystal morphology such that more compact crystals may be produced which can be better separated from the liquid olein phase. The use of CHM's may increase the SE to about 80%, but at the expense of a much increased process time. CHM's slow down both nucleation and crystal growth. Moreover, for the removal of the CHM's from the desired fat fractions additional post-processing is necessary.

Sonocrystallisation is the use of ultrasound for influencing the crystallisation of liquids, either melts or solutions. Ultrasound in common language is sound characterized by a frequency of about 20 kHz and more, extending even into the MHz range. Most applications use ultrasound in the range 20 kHz–5 MHz.

The >20 kHz frequency for defining ultrasound is rather arbitrary and is historically related to the average perception limit of the human ear. Within the context of the present specification such perception limit is irrelevant from a technical point of view. The benefits of the present invention become manifest as well with frequencies well below 20 kHz. In the context of the present specification ultrasound is defined as sound with a frequency of 10 kHz up to 10 MHz.

Since 1927 it is known that by exposing supercooled melts or supersaturated solutions of various substances to ultrasound the nucleation and/or the growth of crystals is remarkably influenced. The effect, sonocrystallisation, was first observed when crystallizing a supersaturated thiosulfate solution. Since then sonocrystallisation has been studied in many other systems. A particular aspect of sonocrystallisation is sononucleation. It deals with the initiation of crystal formation, has been studied extensively with sugar and is applied since the late 50-ties. Sonocrystallisation of supercooled water, supercooled metal melts and supersaturated solutions of various inorganic materials have received a lot of attention in the 50-ties and 60-ties, particularly in Russia.

The crystallisation process can be divided into two stages: crystal nucleation and crystal growth. In the nucleation stage submicroscopic crystal nuclei are formed which develop into larger crystals during the subsequent growth stage. With homogeneous nucleation the crystals are formed directly from the liquid. Heterogeneous nucleation is nucleation mediated by foreign particles already present in the liquid. Secondary nucleation is nucleation mediated by pre-existing crystals. It is believed that the process of the present invention predominantly affects homogeneous nucleation.

Benefits of sonocrystallisation reported in literature include:

Faster nucleation which is fairly uniform throughout the sonicated volume,

Relatively easy nucleation of materials for which nucleation is difficult otherwise, Generation of smaller, purer and more uniform crystals. For literature dealing with sonocrystallisation see the reviews e.g. of Kapustin (Ref.2) and Hem (Ref.3).

When a liquid is exposed to ultrasound, microscopic gas/vapour bubbles are formed which show a dynamic pulsating behaviour. One activity of such ultrasound-induced bubble behaviour is denoted as cavitation. Already at relatively low sound intensities the bubbles do not perish but exhibit stable volume and/or shape oscillations. This type of cavitation is denoted as "stable" or "non-inertial" cavitation. When the ultrasound intensity is increased and exceeds a certain limit, the cavitation threshold, the nature of cavitation changes dramatically which results in the bubbles becoming unstable. Within a fraction of a sound cycle they show rapid growth followed by a violent collapse. The collapsing gas bubbles produce very high pressures and temperatures locally in the bubble as well as a high pressure in the liquid layer surrounding the bubble (see also Hem, 1967, supra).

Cavitation which shows this violent bubble behaviour is denoted as "transient" or "inertial" cavitation (ref.5). By many ultrasound users the terms "cavitation" and "transient cavitation" are used without discrimination.

According to general scientific consensus—which has persisted until now (see e.g. ref. 4 and 8)—the physical mechanism underlying sonocrystallisation and the benefits resulting from it are ascribed to the occurrence of transient cavitation. The prejudice tells that in the absence of transient cavitation the benefits of sonocrystallisation even will not be manifested.

After the 60-ties the scientific attention for sonocrystallisation seems to have decreased. No fundamentally new insights in the believed underlying cavitation mechanism have been reported. However, the technological development and application of ultrasound for the crystallisation of different materials continued.

A few patent applications relate to sonocrystallisation of edible fats. WO 92/20420 describes a method and a device for the control of solidification in liquids. The liquid to be solidified is subjected to inter alia ultrasonic cavitation in order to control the steps of nucleation and/or crystal growth of the solidification process. In conformity with prevailing views the ultrasonic conditions desired for nucleation induction are chosen such that transient cavitation results which implies high intensity ultrasound.

EP 765605 deals with the effect of ultrasonic treatment on fat nucleation. It describes a method for accelerating the polymorphic transformation of edible fat compositions. Such compositions when undercooled by at least 4° C. are exposed to ultrasonic energy for a time and at a frequency sufficient to induce nucleation of stable polymorph crystals without exceeding the melting point of those crystals. Typical fats to be treated by this method are butter fat and the fats used in ice cream, chocolate, margarine and yogurt.

EP 765606 describes a method for retarding fat blooming on chocolate and on other confectionery fat compositions comprising cocoa butter. The method comprises undercooling the molten fat by at least 3° C. below the melting point of the β-polymorph crystal. By exposing it to an effective amount of ultrasonic energy stable crystals are generated.

In those patents cavitation is presented as the evident cause of the enhanced nucleation and the changed crystal morphology.

Traditional sonocrystallisation, however, has shown also serious drawbacks. Sonocrystallisation may trigger sonochemical reactions some of which are believed to cause production of free radicals. Triglyceride fats, especially unsaturated oils, are very susceptible to oxidation damage caused by decomposition of lipo(hydro)peroxides formed by free readicals. The resulting off-flavour and off-taste has become a decisive factor preventing the wide use of sonocrystallisation for edible unsaturated fats. A small flavour defect in the predominantly saturated chocolate fats as exemplified in the patents above is hardly noticed and even less when incorporated in chocolate products. Skilled fat chemists have persisted in believing that sonocrystallisation of an unsaturated edible fat is impossible without adversely affecting its taste and smell.

SUMMARY OF THE INVENTION

We have found that the beneficial effects of fat sonocrystallisation being necessarily related to transient cavitation are based on a prejudice.

The present inventors have found that sonocrystallisation can considerably enhance the nucleation rate of fat crystallisation also when applied in the absence of transient cavitation. Adverse sonochemistry with its flavour spoiling effects does not occur. A major accomplishment was the significant improvement of the separation efficiency of a dry fractionated oxidation sensitive fat without the expected oxidation damage and without adversely affecting the taste and smell of the obtained fat fractions (see example 4).

Generally, the present invention provides a process for the crystallisation of a solid phase from a liquid which liquid is subjected to ultrasound, where the exposure to ultrasound is at such conditions that transient cavitation is absent and for a time and at a frequency sufficient to induce nucleation of stable crystals in the liquid.

DETAILS OF THE INVENTION

Figure 1:
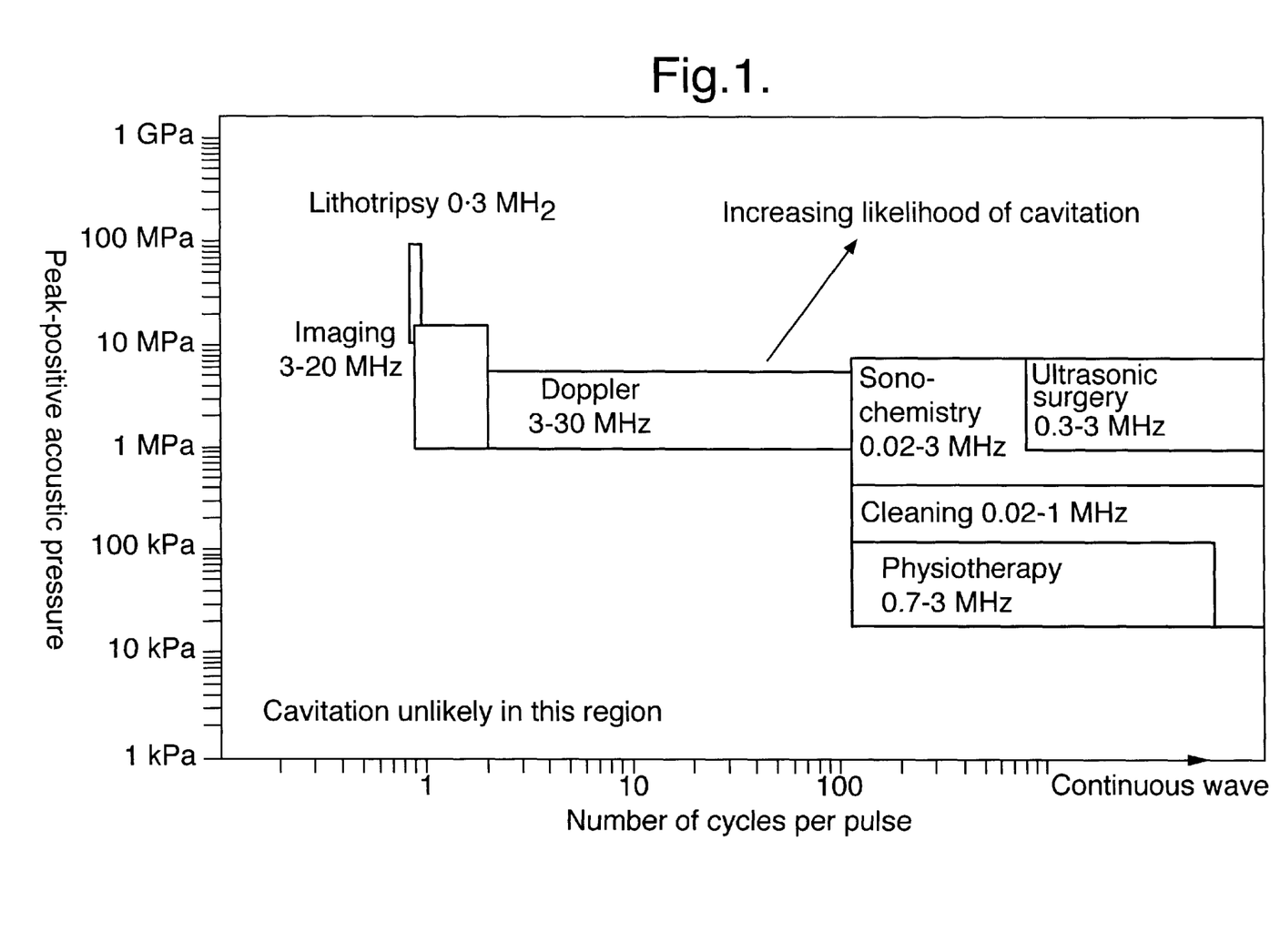
FIG. 1. Is a diagram showing various applications of high power ultrasound, ranging (along the Y-axis) from low to high sound intensity and (along the X-axis) from relatively low frequencies to high frequencies.

Generally, transient cavitation does not occur at low ultrasound intensities. When the sound intensity is increased, eventually the transient cavitation threshold will be exceeded. As is discussed in several sources (see e.g. refs. 7 and 9), the occurence of transient cavitation depends primarily on the intensity of the sound energy but also on several other factors. The frequency of the ultrasound, the temperature and viscosity of the liquid, the amount of dissolved gas, and the presence of surface-active substances affecting the surface tension of the bubbles are the most important secondary factors. FIG. 1 illustrates the zones where for the various applications of ultrasound transient cavitation is likely to occur. The X-axis shows the sound frequency and the Y-axis the sound intensity. For applications situated in the top right corner transient cavitation is always present, for applications shown in the bottom left corner cavitation is always absent. A generally applicable and sharply defined borderline for distinguishing the intensity threshold can not be given. However, in an operational situation with a chosen frequency sound intensities where transient cavitation will not occur can be easily found with some trials. As will be discussed below for each operational situation indicators are available with which it is possible to distinguish wether sonication of a liquid finds place in the presence or in the absence of cavitation. With the colloquial expression "subcavitational conditions" when used for sonication, the substantial absence of transient cavitation throughout the whole volume of crystallizing liquid is meant.

A practical indicator for the absence of transient cavitation is the value of the mechanical index (MI) of the actual ultrasound generating system. The MI is defined as $$MI=(p_{NEG}[MPa])/\sqrt{\sqrt{f[MHZ]}}$$

where $p_{NEG}$[MPa] is the amplitude of the acoustic pressure of the ultrasound field (the pressure amplitude) and f[MHz] is the ultrasound frequency. The MI is used as a risk indicator for indicating the worst-case likelihood of occurring inertial cavitation. It has been adopted by the American Institute of Ultrasound in Medicine as a real-time output to estimate the potential risk of cavitation so that it can be avoided during diagnostic in vivo ultrasound scanning (ref. 5). According to Apfel and Holland (ref.7) transient cavitation does not occur when the MI of the applied system does not exceed the threshold value 0.7. Hence, frequency and pressure amplitude of the ultrasound preferably is chosen such that said threshold value is not exceeded. Since the sound intensity (I) is related to the pressure amplitude $p_{NEG}$ according to the function $$I=p_{NEG}^2/2\rho c$$

the ultrasound intensity should not exceed the corresponding intensity threshold value, where ρ (rho) is the liquid density and is c the velocity of sound, which values in fat are about 920 kg/m$^3$ and 1400 m/s respectively (and in water are hardly different).

The MI based threshold indicator is meant to distinguish riskless, medically safe sonication conditions from conditions where dangerous transient cavitation might, but not necessarily will occur. It precisely indicates the absence of transient cavitation, but less precisely indicates the presence of transient cavitation.

An alternative common and practical way for detecting the presence of transient cavitation is the observation of "sonoluminescence", which is the emission of very short light flashes caused by collapsing cavitation bubbles in the presence of certain chemicals (ref. 6). The method is not preferred, however, for clearly establishing the absence of transient cavitation.

Most suitably, however, the occurrence of transient cavitation can be detected by monitoring with a hydrophone the sound radiated by an ultrasonication cell. The hydrophone is a device which transforms sound energy emitted from a sonication cell into oscilloscope views. The man skilled in the art of reading such views, will easily recognize the onset of transient cavitation by the appearance of peaks of characteristic harmonics and subharmonics and eventually the appearance of "noise" which belongs to full cavitation. The harmonics and sub-harmonics result from the non-linear volume oscillations of strongly driven cavitation bubbles. The shock waves produced by imploding bubbles become visible because they create broad-band pulses in the frequency spectrum. The superposition of many such signals from all bubble implosions generated by a cavitating sound field gives rise to a broad-band "noise" signals pattern. Hence, such noise pattern points to the many violent bubble collapses which are characteristic for transient cavitation. By contrast, bubble oscillations during stable, non-transient cavitation do not show a noise pattern in the hydrophone view (ref. 9).

The sonocrystallisation process of the present invention employs such low intensity ultrasound that a hydrophone, when detecting sound radiated from the ultrasound exposed liquid, shows a signals pattern which is free from broad-band cavitation noise.

A preferred embodiment of the present invention is characterized by the ultrasound intensity being at such low level that a hydrophone when detecting sound radiated from the ultrasound exposed liquid shows a view with a main signal corresponding with the main radiation frequency and a further signal corresponding with the first subharmonic frequency where the intensity peaks ratio of the further signal and the main signal, the peaks ratio $A_S/A_F$, is <0.5.

Most preferably the ultrasound intensity is at such low level that a hydrophone when detecting sound radiated from the ultrasound exposed liquid shows a view with a single signal corresponding with the main radiation frequency without substantially showing additional signals corresponding with subharmonics frequencies.

It should be noted that the claimed condition "In the absence of transient cavitation" includes conditions with the occasional occurrence of transient cavitation. Such occasional cavitation does not give rise to the noise pattern as detectable by a hydrophone and equally will not have an adverse effect on the sensoric properties of the treated fat.

It should be further noted that the intensity of the energy radiating from an ultrasound probe is fading away with an increasing distance from the energy source. At a relatively large distance from the probe cavitation is always absent. In a large volume of liquid cavitation may occur near the ultrasone probe while at the same time cavitation is absent at remote places of the same liquid. Therefore the criterion of the present invention is that transient cavitation is absent throughout the whole volume of the sonicated liquid.

Processing conditions other than the ultrasound intensity such as time and temperature and frequency as mentioned before can easily be optimized by the skilled person by some trials. It has been found, e.g., that for ultrasound crystallisation of anhydrous milk fat the intensity optimum is just below the cavitation threshold (example 4). Generally, a too long exposure of the crystallized fat to ultrasound may cause a collapse of the crystal structure. Sonocrystallisation is particularly effective when cooling has proceeded so far that the system has become supersaturated.

In principle, the present invention is suitable for the sonocrystallisation of all kinds of liquids. It has been found to be particularly useful for sonocrystallisation of triglyceride oils either being of vegetable or of animal origin or being a mixture of both. Preferably, the triglyceride oil is of vegetable origin and is selected from the group consisting of rapeseed oil, palmkernel oil, sunflower oil, groundnut oil, mustard oil, safflower oil, sesame oil, corn oil, soybean oil, cottonseed oil, linseed oil and olive oil. Oils having an animal origin include marine oils and milk fat. All those fats are more or less unsaturated and are susceptible for adverse sonochemistry and flavour deterioration when treated by traditional sonocrystallisation.

Some fats are solid at ambient temperature and have to be liquefied by heating before a dry fractionation process can be carried out. Most of the mentioned vegetable fats are liquid and do not need an initial liquefying step.

Preferably the fats are unmodified, but also modified fats such as hydrogenated fats or fats which have been subjected to interesterification will benefit from the present invention.

A preferred embodiment of the present invention is a process for fractionating a triglyceride fat, which comprises the steps of:
a. when the fat is solid, heating the triglyceride fat until no substantial amount of solid triglyceride fat is present in the oil,
b. allowing the triglyceride oil to cool and to crystallize resulting in a solid stearin fraction and a liquid olein fraction,
c. recovering the stearin fraction by separating it from the olein fraction, characterised in that during step b. the oil is exposed to ultrasound in the absence of transient cavitation.

A typical vessel suited for batch fractionation is equipped with proper means for heat exchanging, for stirring the vessel content, for applying ultrasound energy and for monitoring the occurrence of cavitation. It goes without saying that alternative equipments can be arranged with devices which equally will allow the invention to be carried out. The sonication vessel could be filled via a pre-cooling unit; the sonication being started either in that unit or in the tube conducting the liquid to be crystallized to the main crystallisation vessel.

Other embodiments of the invention relate to processes for the preparation of edible emulsion spreads which may be either water continuous or fat continuous. The most common spreads such as margarine have a continuous fat phase and a dispersed aqueous phase. Such spreads are traditionally prepared by passing a mixture of the aqueous phase and the oil phase through a series of one or more scraped-surface heat exchangers and pin stirrers. The oil phase of those mixtures is eventually crystallized by cooling under such shear that a plastic W/O-emulsion is obtained in which a lattice of fine fat crystals provides the desired consistency and stabilizes the dispersed aqueous phase.

Alternatively the process of spread preparation may start with a continuous aqueous phase emulsion and includes a phase inversion step in order to impart fat continuity to the emulsion spread.

The lattice of fat crystals in the spread necessarily consists of solid saturated fat. For reasons of healthy nutrition and economy of raw materials the content of such saturated fat preferably is restricted to the minimal functional amount. The present invention has shown to have such a beneficial influence on nucleation and eventually on the strength of the crystal lattice that even at relatively low solid fat levels a spread product with a good consistency, texture and stability is obtained.

Consequently the present invention provides a process for the preparation of a fat continuous emulsion spread comprising the steps of a. mixing a liquefied fat phase comprising essentially no solid fat and an aqueous phase so that a water-in-oil emulsion results, b. cooling and working the emulsion to cause partial crystallisation of the fat until a desired consistency and texture is obtained, characterised in that in the step comprising fat crystallisation the emulsion is exposed to ultrasound in the absence of transient cavitation.

Alternatively, the present invention further provides a process for preparing a W/O-emulsion spread comprising the steps of a. preparing an O/W-emulsion having a continuous aqueous phase containing dispersed fully liquefied fat, cooling the emulsion to cause partial crystallisation of the fat, so obtaining a dispersion of partially crystallized fat in a continuous aqueous phase, b. inverting the O/W-emulsion into a fat continuous emulsion in the usual way, c. working and cooling the fat continuous emulsion to cause further partial crystallisation of the fat until a desired consistency and texture is obtained, characterized in that in the step comprising fat crystallisation the emulsion is exposed to ultrasound in the absence of transient cavitation.

For present spread manufacturing processes the invention is most beneficial for the preparation of emulsion spreads which are fat continuous. Proper fat crystallisation plays, however, also a role in the preparation of spreads in which fat is the dispersed phase and where sonocrystallisation according to the present invention also is a most beneficial tool.

A since long acknowledged benefit of sonocrystallisation is its potential influence on the habitus of the crystallized fat. The formation of one fat polymorph may be promoted over another one. Since some polymorphs possess preferred properties, sonocrystallisation provides a tool for improving the properties of the resulting fat and indirectly for improving the properties of food products containing those triglyceride fats.

It should be noted that the invented sonication treatment is a new tool for fat modification that creates the chance but not the guarantee of improved nucleation or of the formation of a SE enhancing crystal morphology.

Processes, ingredients and equipment for fat fractionation and for the preparation of said emulsion spreads, the fat continuous as well as the water continuous ones, are well known by the person skilled in the art and can be found with all details in various textbooks such as K. A. Alexandersen, Margarine Processing Plants and Equipment (Vol.4, Bailey's Industrial Oil and Fat Products, Wiley and Sons Inc., New York 1996).

EXAMPLES

Figure 2:
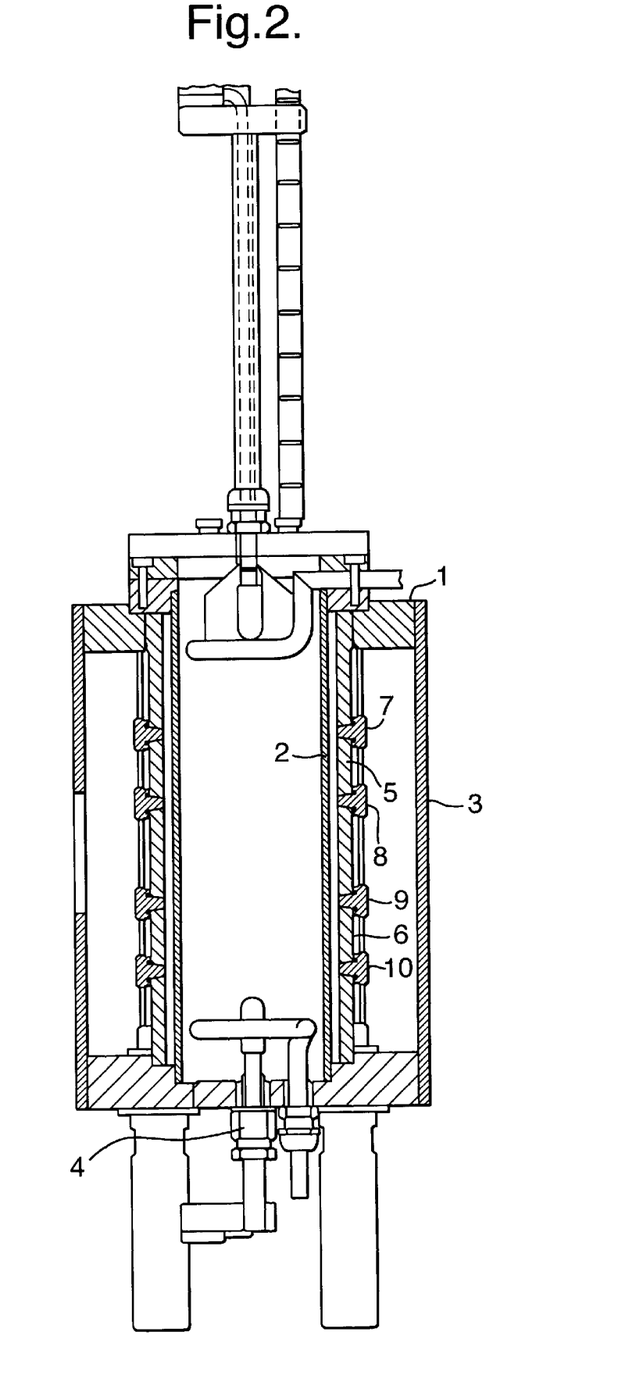
FIG. 2. Shows an experimental ultrasonic vessel component assembly where various conditions which determine cavitation can be varied.

Besides a commercial ultrasound probe geared to generate transient cavitation sound, we used for the exposure of the following exemplified samples to ultrasound the experimental device as illustrated by FIG. 2.

It comprises a vessel 1 comprising an inner perspex jacket 2 and an outer perspex jacket 3. The vessel 1 is generally cylindrical and closed at both ends. A thermocouple arrangement 4 projects into the body of vessel 1 through one of the ends. The thermocouple is combined with a hydrophone arrangement to monitor the emitted ultrasound.

At the other end of vessel 1 cooling/heating coils and also a blade stirrer project into the body of the vessel.

For generating ultrasound two circular transducers 5 and 6 are located circumferentially around the periphery of the inner perspex jacket 2. These are held in place by alignment rings 7, 8, 9 and 10.

The ultrasound is generated and controlled by readily available standard equipment. It adjusts the frequency and intensity of the ultrasound as appropriate.

The installed transducer is capable of operating both below and above the cavitation intensity threshold. The cell is further provided with means for controlling the temperature of the sample and for delivering the sound energy either continuously of pulse-wise.

While monitoring the hydrophone the frequency of the ultrasound in the device of FIG. 2 is adjusted such that a suitable resonant ultrasound frequency is found and maintained. Particularly the 10–11 kHz region is suited.

Example 1

This example and the next one are meant to compare sonocrystallisation of triglyceride oil samples with and without transient cavitation and to show that cavitation induced sonochemistry is actually related to the occurrence of off-flavours.

The test uses ultrasound generated by a common commercial Branson™ probe. Like the majority of industrial ultrasonic probes it is meant to produce high intensity fields at relatively low frequencies so that the believed beneficial cavitational bubble clouds are generated in the exposed material. A high intensity sound energy burst is emitted at a frequency of 20 kHz.

Refined sunflower oil was exposed to ultrasound using the lowest power output of 30 W of this ultrasound device, the exposure time varying from 1 to 10 minutes.

The sonication cell was maintained at 20° C. and samples were stirred at a constant rate.

For detecting the expected sonochemical changes mass spectroscopy was used as the instrumental method, supplemented with sensoric sniffing of the samples (see also example 2).

Figure 3:
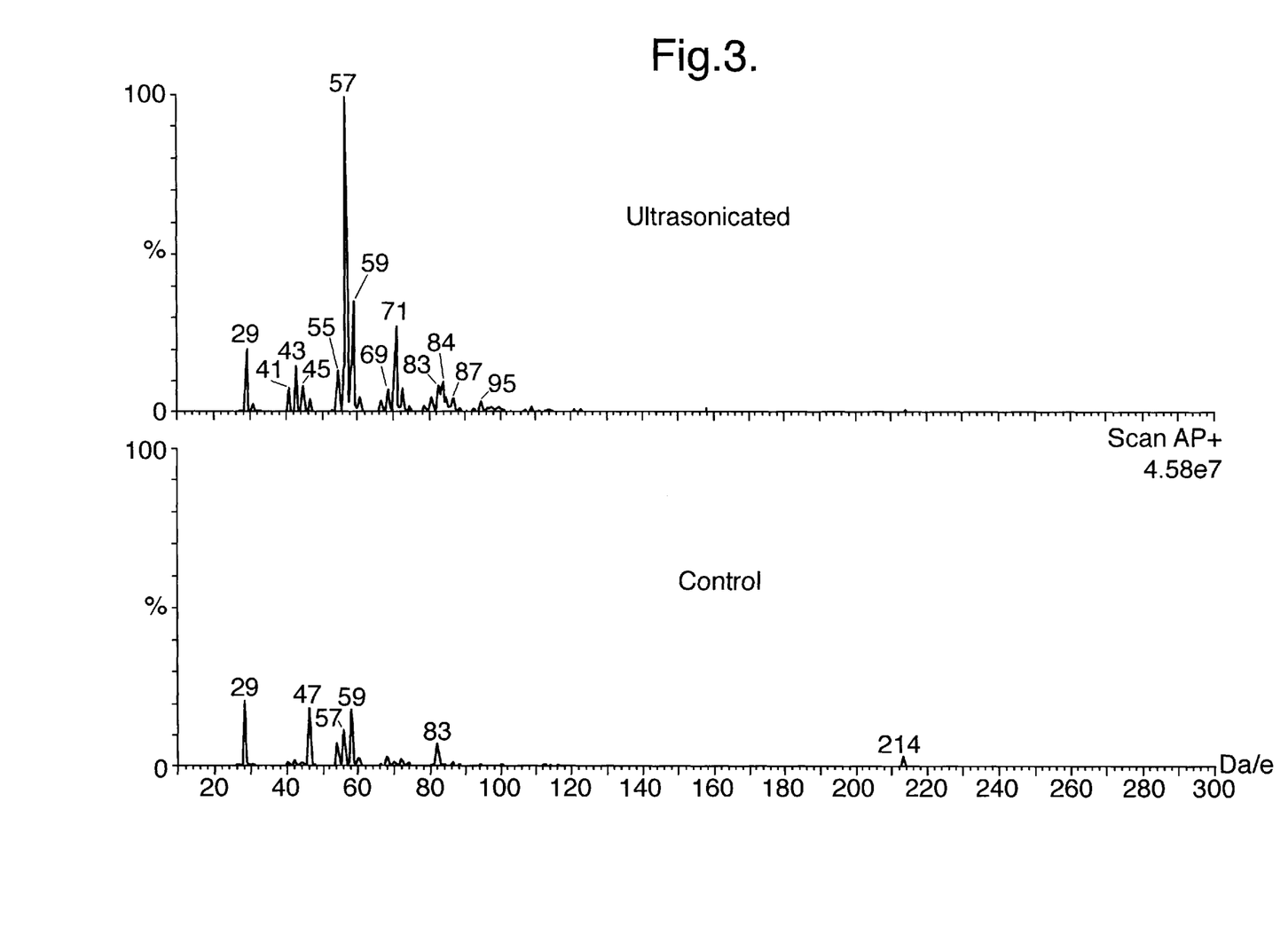
FIG. 3. Is a common mass spectograph showing characteristic peaks of sonicated and non-sonicated sunflower seed oil samples.

FIG. 3 shows the mass spectrum for both the sunflower oil sample sonicated under cavitation conditions and a comparison non-sonicated sample.

Several of the ultrasound-induced mass spectrum peaks of the sonicated sample were recognized as related to known off-flavour compounds by the scientists skilled in testing oils on deterioration. The oil deterioration was further confirmed by a sensory panel test (see also example 2).

When investigating the deterioration effects of sonocrystallisation on triglyceride oil as a function of the sound intensity, frequency, temperature, presence of oxygen, addition of water, metal-ion contamination and storage conditions, it has appeared that the major cause for off-flavour formation was the occurrence of cavitation during sonication.

Example 2

The present example compares triglyceride sonocrystallisation with and without transient cavitation and shows the findings of a sensory panel on the formation of off-flavour. A bland refined sunflower oil was divided in four samples A, B, C and D. Sample B was the only one not sonicated.

Each of the samples A, C and D was at 20° C. subjected in a sonication cell to the sonication conditions A, C and D:

A. The oil was sonicated for only 3 minutes using the common Branson™ probe which is meant to generate transient cavitation.

C. The oil was sonicated for one hour in the device of FIG. 2 at a sound intensity near the cavitation threshold. Only occasionally transient cavitation occurred.

D. The oil was sonicated for one hour in the device of FIG. 2 at a sound intensity for which not any transient cavitation could be observed.

The occurrence of transient cavitation was monitored using a hydrophone.

Each of the three sonicated samples was submitted to a sensoric panel (n=22) for flavour assessment. Each panel member received successively each of the three samples accompagnied by the untreated sunflower sample B without knowing which of both was the untreated sample. Each panel member had to answer the question whether (s)he could perceive a flavour/taste difference between both samples. Table I summarizes the panel response.

TABLE I

Sonicated Oil Panel Assessment (n = 22)

| Sunflower Oil (SF) Sample | No difference | Hesitation or slight difference | Clear difference |
| --- | --- | --- | --- |
| Bland SF not sonicated (comparison) | | | |
| SF 3 min sonicated with transient cavitation (1) | 0 | 0 | 22 (3) |
| SF 1 hour sonicated with occasionally occurring transient cavitation (2) | 17 | 5 | 0 |
| SF 1 hour sonicated without any transient cavitation (2) | 19 | 3 | 0 |

(1) Branson ™ sonication probe used
(2) Device of FIG. 2 used
(3) Flavour characterized as: metal, fishy, off The experiment made clear that an unsaturated oil as sunflower seed oil can be subjected to an ultrasound treatment without substantial damage to flavour and taste.

Example 3

Sonocrystallisation in the Absence of Transient Cavitation

This example demonstrates that in contrast to general belief also in the absence of transient cavitation sononucleation can be demonstrated.

This time the chosen sound frequencies are in the MHz area which are common for medical applications (see FIG. 1).

A blend of 12% hydrogenated palm oil dissolved in 88% sunflower oil of 60° C. was divided in two samples (a) and (b). Both were poured into an ultrasound cell according to FIG. 2 and continuously cooled. From 45° C. downwards sample (b) was exposed to continuous 1.5 MHz ultrasound at an intensity of 1.5 W/cm$^2$. Sample (a) was cooled in the same way but without sonication.

Figure 4:
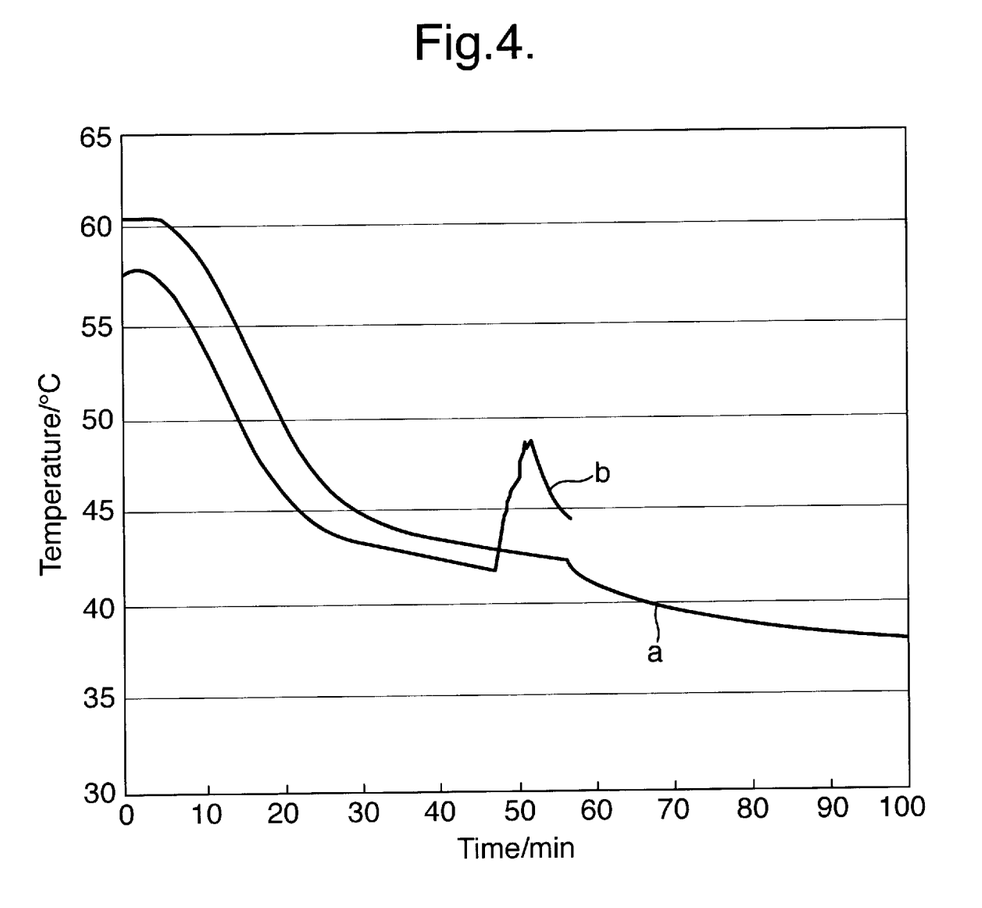
FIG. 4. Depicts the time/temperature profiles of two fat blend samples during cooling.

FIG. 4 shows the temperature graphs of both samples during the cooling period.

After 50 minutes of cooling a sudden temperature rise in sample (b) occurred which is ascribed to the release of heat of crystallisation at the onset of fat crystallisation. Ten minutes after the occurrence of that peak the sample became turbid of fat crystals. At that time sample (a) did not yet show any fat crystallisation.

The sonication was monitored with a hydrophone which only had shown (FIG. 5) the single peak 1.5 MHz peak of the ultrasound sound frequency which means that transient cavitation had been absent.

The MI value being 0.09, is far below the transient cavitation threshold of 0.7, which further confirms the absence of cavitation.

Figure 5:
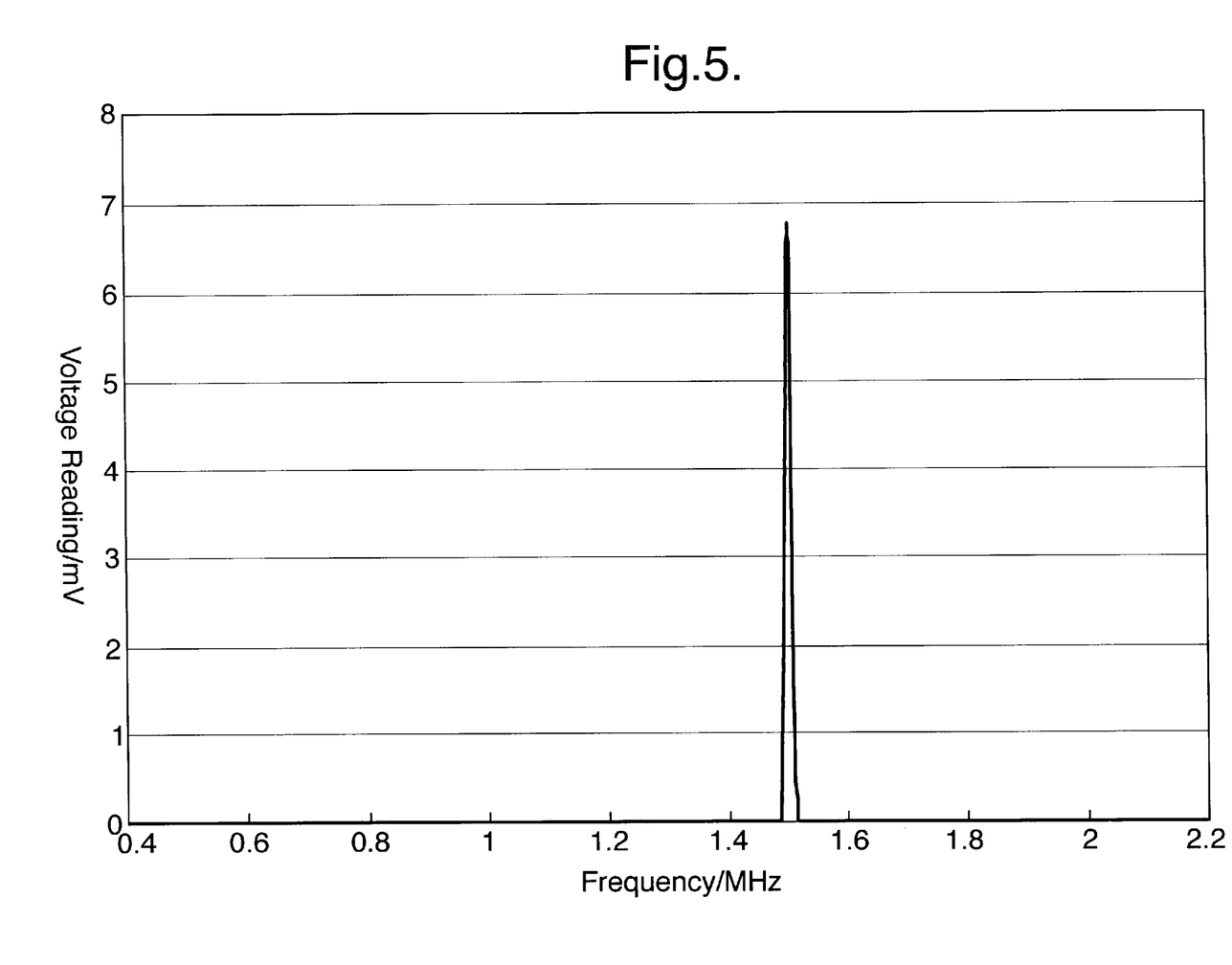
FIG. 5. Shows for a sonicated oil sample the single hydrophone signal at 1.5 MHz frequency and at 1.5 W/cm2 intensity where besides the peak of the fundamental frequency no peaks of harmonics are visible. This hydrophone view is characteristic for the absence of transient cavitation.
Figure 6:
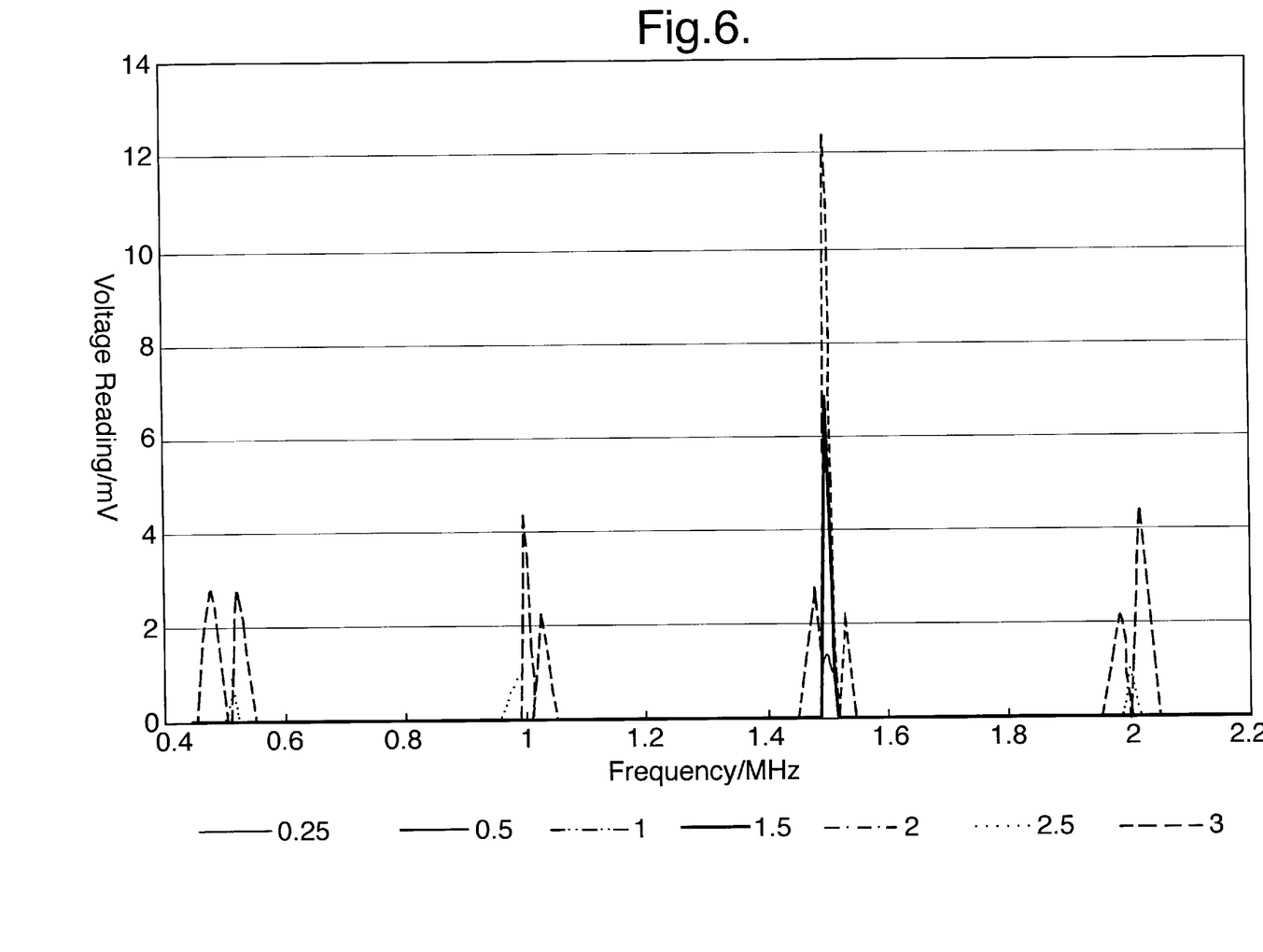
FIG. 6. Shows for a sonicated oil sample, in contrast to FIG. 5, the onset of subharmonics at 1.5 MHz where the sound energies have increased to such extent that the cavitation threshold has been exceeded.

FIG. 6 shows in contrast with FIG. 5 a hydrophone view of high intensity ultrasound sonication where the cavitation threshold had been exceeded. That transient cavitation prevails is apparent from the various of (sub)harmonics peaks.

Example 4

Fat Fractionation With the Use of Ultrasound

Butterfat (AMF, anhydrous milk fat) was obtained from Corman. The fat was melted and, while stirring (50 rpm), was kept at 65° C. for at least 1 hour to ensure thorough melting and to avoid so-called "memory effect". Subsequently it was cooled to 40° C. in one hour and then to 33° C. at 5° C./h. Only after the final temperature was reached sonication without transient cavitation was applied on the supersaturated sample for 15 minutes (65 kHz, 30 dB). Then the sample was kept overnight at 33° C. without stirring to let the crystallisation process proceed to completion. The crystals were vacuum filtered (factor 3 ceramic filter) for 30 minutes and then pressed. The pressure was gradually increased to 12 bar over a period of 60 minutes.

The anhydrous milk fat (AMF) commonly is dry fractionated with a separation efficiency of 60%. Table II shows that use of ultrasound gave a SE of 80%, a spectacular improvement over the control. The hydrophone at no time showed the occurrence of transient cavitation. The flavour quality of the crystallised fat was not affected.

TABLE II

| Sample | Dispersion Solids % | Filtered Solids % | Pressed Solids % (12 bar) |
| --- | --- | --- | --- |
| Control 1 | 8.7 | 18.7 | 60.7 |
| Control 2 | 9.1 | 22.1 | 60.8 |
| 15 min at 33° C. 1 | 7.1 | 18.7 | 78.8 |
| 15 min at 33° C. 2 | 8.1 | 21.0 | 82.3 |

The experiment was repeated with other ultrasonic intensities, but all in the absence of transient cavitation. The intensity optimum for sononucleation appeared to be just below the cavitation threshold.

Ultrasound caused a dramatic effect on crystal size, shape and distribution. The textures of the final fat fractions appeared to be very different from each other as well as from the non-sonicated control sample. This example proves that kinetics and structure of fat crystals may be greatly affected by exposure to ultrasound even in the absence of transient cavitation.

REFERENCES

1. Hamm, Trans. IChemE. 74C, 1996, 61.
2. Kapustin, The effects of ultrasound on the kinetics of crystallisation; Consultants Bureau, New York, 1963.
3. Hem, The effect of ultrasonic vibrations on crystallisation processes; Ultrasonics, October 1967, p. 202.
4. Kallies, Zur gezielten Suspensionserzeugung für die Konfektionierung von Schmelzen; PhD Thesis, Bremen 1995.
5. Leighton T. G., The principles of cavitation; chapter 9 in "Ultrasound in Food Processing", (Povey & Mason, eds.) Blackie Academic & Professional, London (1998).
6. Crum L. A., Sonoluminescence, sonochemistry and sonophysics, J. Acoust. Soc. Am. 95(1), 1994, 559.
7. Apfel R. E., Holland C. K., Gauging the likelihood of cavitation from short-pulse low-duty cycle diagnostic ultrasound, Ultrasound Med. Biol. 17, 1991, 179.
8. Internetsite http://www.aeat.com/sono/, particularly "How does it work" under "Frequently Asked Questions". Printed on Mar. 21, 2001.
9. Gélat P., Hodnett M, Zeqiri B., Establishing a reference ultrasonic cleaning vessel: part 1: Supporting infrastructure and early measurements, National Physical Laboratory Report CMAM 55, September 2000.

What is claimed is:

1. A process for the crystallization of a solid fat phase from a liquid comprising subjecting the liquid to ultrasound, where the exposure to ultrasound is at such conditions that transient cavitation is absent and for a time and at a frequency sufficient to induce nucleation of stable crystals in the liquid, where the ultrasound intensity is adjusted at such low level that a hydrophone, when detecting sound radiated from the ultrasound exposed liquid, shows a view which is free from broad-band cavitation noise signals pattern.

2. A process according to claim 1, where ultrasound intensity is at such low level that a hydrophone when detecting sound radiated from the ultrasound exposed liquid shows a view with a main signal corresponding with the main radiation frequency and a further signal corresponding with the first subharmonic frequency where the intensity peaks ratio of the further signal and the main signal is <0.5.

3. A process according to claim 1, where ultrasound intensity is adjusted at such low level that a hydrophone when detecting sound radiated from the ultrasound exposed liquid shows a view with a single signal corresponding with the main radiation frequency without substantially showing additional signals corresponding with subharmonics frequencies.

4. A process according to claim 1, where an ultrasound generating system is used of which the mechanical index (MI) is <0.7, where $$MI = (p_{NEG}[MPa])/\sqrt{f[MHz]}$$

and where $p_{NEG}$[MPa] is the amplitude of the acoustic pressure of the ultrasound field (the pressure amplitude) and f[MHz] is the ultrasound frequency.

5. A process according to claim 1, where the liquid is a triglyceride oil of vegetable or animal origin or a mixture of both.

6. A process according to claim 5, where the triglyceride oil of vegetable origin is selected from the group consisting of rapeseed oil, palmkernel oil, sunflower seed oil, groundnut oil, mustard oil, safflower oil, sesame oil, corn oil, soybean oil, cottonseed oil, linseed oil and olive oil.

7. A process according to claim 5, where the triglyceride oil is a liquefied dairy fat.

8. A process for fractionating a triglyceride oil, which comprises the steps of:
   a. when the fat is solid, heating the triglyceride oil until no substantial amount of solid triglyceride is present in the oil;
   b. allowing the triglyceride oil to cool and to crystallize resulting in a solid stearin fraction and a liquid olein fraction;
   c. recovering the stearin fraction by separating it from the olein fraction,
   where during step b. the oil is exposed to ultrasound in the absence of transient cavitation.

9. A process for the preparation of a fat continuous emulsion spread comprising the steps of
   a. mixing a liquefied fat phase comprising essentially no solid fat and an aqueous phase so that a water-in-oil emulsion results;
   b. cooling and working the emulsion to cause partial crystallisation of the fat until a desired consistency and texture is obtained,
   where in the step comprising fat crystallisation the emulsion is exposed to ultrasound in the absence of transient cavitation.

10. A process for preparing a W/O-emulsion spread comprising the steps:
   a. preparing a O/W-emulsion having a continuous aqueous phase containing dispersed fully liquefied fat cooling the emulsion to cause partial crystallisation of the fat, so obtaining a dispersion of partially crystallized fat in a continuous aqueous phase;
   b. inverting the O/W-emulsion into a fat continuous emulsion,
   c. working and cooling the fat continuous emulsion to cause partial crystallisation of the fat until a desired consistency and texture is obtained,
   where in the step comprising fat crystallisation the emulsion is exposed to ultrasound in the absence of transient cavitation.

11. A process for preparing a O/W-emulsion spread comprising the steps:
   a. preparing a O/W-emulsion having a continuous aqueous phase and a dispersed fully liquefied fat phase and cooling the emulsion to cause partial crystallisation of the fat, so obtaining a dispersion of partially crystallized fat in a continuous aqueous phase;
   b. working and cooling the fat continuous emulsion to cause partial crystallisation of the fat until a desired consistency and texture is obtained,
   where in the step comprising fat crystallisation the emulsion is exposed to ultrasound in the absence of transient cavitation.

* * * * *